(12) United States Patent
Bayer et al.

(10) Patent No.: US 6,806,066 B2
(45) Date of Patent: Oct. 19, 2004

(54) EXPRESSION VECTORS WITH MODIFIED COLE1 ORIGIN OF REPLICATION FOR CONTROL OF PLASMID COPY NUMBER

(75) Inventors: Karl Bayer, Vienna (AT); Reingard Grabherr, Pressbaum (AT); Erik Nilsson, Linkoeping (SE); Gerald Striedner, Vienna (AT)

(73) Assignee: Boehringer Ingelheim International GmbH (DE)

( * ) Notice: Subject to any disclaimer, the term of this patent is extended or adjusted under 35 U.S.C. 154(b) by 0 days.

(21) Appl. No.: 09/969,136

(22) Filed: Oct. 3, 2001

(65) Prior Publication Data

US 2003/0166053 A1 Sep. 4, 2003

(30) Foreign Application Priority Data

Oct. 4, 2000 (EP) .............................................. 00121709

(51) Int. Cl.[7] .......................... C12P 21/00; C07H 21/04; C12M 15/00
(52) U.S. Cl. ..................... 435/71.2; 435/320.1; 536/24.1
(58) Field of Search .............................. 435/71.2, 320.1; 536/24.1

(56) References Cited

FOREIGN PATENT DOCUMENTS

WO     WO 89/07141     8/1989

OTHER PUBLICATIONS

Dooley et al. Isolation and characterization of mutants affecting functional domains of ColE1 RNAI. J Mol Biol. Nov. 5, 1985;186(1):87–96.*

Cesareni, G. et al., "Control of ColE1 plasmid replication by antisense RNA," *Trends Genet.* 7:230–235, Elsevier Science Publishers Ltd. (1991).

Chan, P.T. et al., "Nucleotide Sequence and Gene Organization of ColE1 DNA," *J. Biol. Chem.* 260:8925–8935, The American Society for Biochemistry and Molecular Biology (1985).

Gultyaev, A.P. et al., "The influence of a metastable stucture in plasmid primer RNA on antisense RNA binding kinetics," *Nucleic Acids Res.* 23:3718–3725, Oxford University Press (1995).

Hjalt, T. and Wagner, E.G.H., "The effect of loop size in antisense and target RNAs on the efficiency of antisense RNA control," *Nucleic Acids Res.* 24:6723–6732, Oxford University Press (1992).

Lin–Chao, S. and Cohen, S.N., "The Rate of Processing and Degradation of Antisense RNAI Regulates the Replication of ColE1–Type Plasmids In Vivo," *Cell* 65:1233–1242, Cell Press (1991).

Merlin, S. and Polisky, B., "Assessment of Quantitative Models for Plasmid ColE1 Copy Number Control," *J. Mol. Biol.* 248:211–219, Academic Press Limited (1995).

Tomizawa, J.–i., "Control of ColE1 Plasmid Replication: Initial Interaction of RNA I and the Primer Transcript Is Reversible," *Cell* 40:527–535, Cell Press (1985).

Tomizawa, J.–i., "Control of ColE1 Plasmid Replication. Intermediates in the Binding of RNA I RNA II," *J. Mol. Biol.* 212:683–694, Academic Press Limited (1990).

Wróbel, B. and Wegrzyn, G., "Replication Regulation of ColE1–like Plasmids in Amino Acid–Starved *Escherichia coli,*" *Plasmid* 39:48–62, Academic Press, Inc. (1998).

Yavachev, L. and Ivanov, I., "What Does the Homology Between *E. coli* tRNAs and RNAs Controlling ColE1 Plasmid Replication Mean?" *J. Theor. Biol.* 131:235–241, Academic Press Limited (1988).

NCBI Entrez, GenBank Report, Accession No. NC—001371, Tomizawa, J.I. et al. (Apr. 2000).

* cited by examiner

*Primary Examiner*—Anne-Marie Falk
*Assistant Examiner*—Daniel M. Sullivan
(74) *Attorney, Agent, or Firm*—Sterne, Kessler, Goldstein & Fox P.L.L.C.

(57) ABSTRACT

In an expression vector having a ColE1 replication system, the homology of the RNAI and RNAII of the ColE1 origin of replication to uncharged tRNAs is modified mutations in the coding region of the RNAI gene and corresponding mutations in the RNAII gene. The mutation results in one or more base exchanges in loop 1 and/or loop 2 and/or loop 3 of RNAI and RNAII. In methods using this vector for producing recombinant proteins, plasmid copy number is stably maintained. In methods for plasmid production, high plasmid copy numbers can be obtained.

14 Claims, 1 Drawing Sheet

Figure 1:
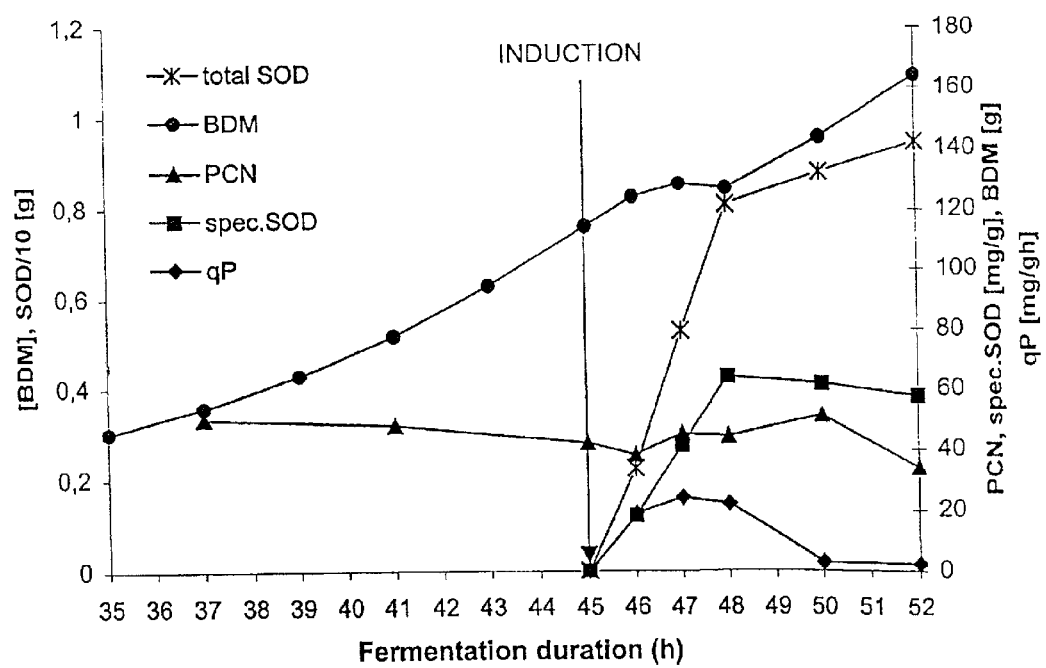

EXPRESSION VECTORS WITH MODIFIED COLE1 ORIGIN OF REPLICATION FOR CONTROL OF PLASMID COPY NUMBER

CROSS-REFERENCE TO RELATED APPLICATIONS

This application claims priority benefit of European Application No. EP 00 121709.0, filed Oct. 4, 2000, the contents of which are incorporated herein by reference.

BACKGROUND OF THE INVENTION

1. Field of the Invention

The present invention relates to improved expression vectors having a ColE1 origin of replication system, for the production of recombinant proteins and plasmid DNA.

2. Related Art

The use of fermentation processes with genetically modified microorganisms (GMO) for the production of recombinant proteins of interest or for producing plasmid DNA has become widespread in industry.

When optimizing a fermentation process the major goal is to obtain as much product as possible, with good quality, in a cost-effective way. To achieve this, the volumetric productivity, defined as units of product formed per volume and time, needs to be optimized. Factors with great impact on the optimization process are the biomass per volume, i.e., the amount of cells capable of producing the product, and the quantity of protein each cell can produce. To a certain limit, the production capacity per cell is proportional to the plasmid copy number (PCN), the number of plasmids in the cell carrying the gene coding for the recombinant protein. Furthermore, the strength of the transcription system for the recombinant protein is important. While some promoters are weak and do not take full advantage of the metabolic potential, many promoters are too strong and lead to overexpression of the recombinant protein. Since the metabolic resources have to be shared between the expression of the recombinant protein and the host protein, an expression system which is too strong, will soon lead to a depletion of the metabolic resources, which results in cell death.

Recently, the use of plasmid DNA in the field of gene therapy has become the focus of a whole new industry. Therefore, sufficient amounts of high quality plasmid DNA are required. In plasmid production processes, no recombinant protein is produced; instead, the cell factory is exploited for plasmid DNA production. Extremely high plasmid replication rates are necessary in order to achieve this goal, whereby the host cell has to accomplish tasks that differ from recombinant protein production.

For bacterial fermentation processes, ColE1 plasmids have been suggested mainly because high plasmid copy numbers can be obtained using this system.

ColE1 plasmids have been extensively described previously (Chan, P. T., et al., *J. Biol. Chem.* 260:8925–35 (1985)), and the replication mechanism of ColE1 origin of replication has been well studied (Cesareni, G., et al., *Trends Genet.* 7:230–5 (1991)). Replication from a ColE1 plasmid starts with the transcription of the preprimer RNAII, 555 bp upstream of the replication origin by the host's RNA polymerase (Tomizawa, J., *Cell* 40:527–535 (1985)). RNAII folds into specific structures during elongation and after polymerization of about 550 nucleotides begins to form a hybrid with the template DNA. The preprimer transcription terminates heterogeneously and after hybrid formation the RNAII preprimer is cleaved by RNase H to form the active primer with a free 3' OH terminus, which is accessible for DNA polymerase I (Tomizawa, J., *J. Mol. Biol.* 212:683–694 (1990); Lin-Chao, S. and Cohen, S., *Cell* 65:1233–1242 (1991); Merlin, A. and Polisky, B., *J. Mol. Biol.* 248:211–219 (1995)).

The ColE1 region contains two promoters. RNAI is an antisense RNA molecule of 108 nucleotides, which is transcribed from the second promoter on the opposite strand and is complementary to the 5' end of RNAII. RNAI is transcribed from 445 bp upstream from the replication origin, to about where the transcription of RNAII starts (Merlin, A. and Polisky, B., *J. Mol. Biol.* 248:211–219 (1995); Tomizawa, J., *J. Mol. Biol.* 212:683–694 (1990)).

For regulation of plasmid copy number in ColE1 plasmids, the kinetics is more important than the equilibrium features. For example, some mutant strains with mutations in the RNAII, although not influencing the regions complementary to RNAI, result in decreased inhibition by RNAI. This is probably due to affecting the half-life of intermediate RNA structures, decreasing the time for RNAI susceptibility, and hence resulting in increased plasmid copy numbers. This finding suggests the importance of intermediate RNAII structures and kinetics of RNAII folding pathway (Gultyaev, A., et al, *Nucleic Acids Res.* 23:3718–25 (1995)).

It has been observed that starvation of amino acids results in large amounts of tRNAs that are not charged with the specific amino acid. (In the following, these tRNAs are termed "uncharged tRNAs".) This phenomenon can be compared with the situation at the time after induction of recombinant protein expression, when the metabolic resources are depleted, as discussed above.

Wróbel, B. and Wegrzyn, G., *Plasmid* 39:48–62 (1998) tested a strategy of selectively inducing starvation of five different amino acids. It was found that there is a positive correlation between the homology of the anticodon loops of the tRNAs corresponding to the particular deprived amino acids, and particular loops in RNAI and RNAII. It was assumed that most of the charged tRNAs are captured by the translation mechanism, but that the uncharged tRNAs could instead have a chance to interact with other molecules, the RNAI and RNAII. Interaction between tRNA and RNAI or RNAII would most probably interfere with the interaction between RNAI and RNAII, resulting in a higher RNAII-DNA hybridization frequency (supposed that the tRNA interacting with RNAII does not change the RNAII structure in any drastic way). The latter would imply a higher replication frequency and thus a higher PCN.

Zavachev, L. and Ivanov, I., *J. Theor. Biol.* 131:235–241 (1988) compared the homology between all 21 tRNAs and RNAI/RNAII. Of these, 11 showed a homology greater than 40% to either RNAI or RNAII. They divided these into three categories: a) tRNAs homologous to RNAI: Arg, His, Leu, Lys, Phe and Thr, b) tRNAs homologous to RNAII: f-Met, Try and Gly and c) tRNAs homologous to both RNAI and RNAII: Met and Val. All tRNAs have anticodon loops of 7 nucleotides (Hjalt, T., et al., *Nucl. Acids Res.* 24:6723–32 (1992)). In the case with tRNAs homologous to RNAI, the highest homology was found in the region of loop 2, while most showed less homology in the 5' end of RNAI.

Starvation and cellular stress lead to increased pools of uncharged tRNAs, which interact with the origin of replication of ColE1 plasmids. This interaction occurs due to the tRNAs' sequence homology to three RNA-loop structures, present in RNAI and RNAII of the origin of replication, which leads to interference with the PCN control mechanism of the system. Thus, PCN increases rapidly and causes a breakdown of the fermentation process.

To overcome these problems, International Appl. No. WO 89/07141 suggests an expression vector having a ColE1 replication system, comprising a mutation in the RNAII gene and/or the rop gene with the goal to increase expression. This was achieved without substantially increasing plasmid copy number.

Since a bacterial fermentation process is only efficient when the system can be maintained over an extended period of time and since an increased plasmid copy number is one of the main factors that cause collapse of the expression system, it was an object of the invention to provide an improved expression system with a prolonged bacterial viability during fermentation.

SUMMARY OF THE INVENTION

The present invention relates to an expression vector having a ColE1 replication system, in which the homology of the RNAI and RNAII of the ColE1 origin of replication to uncharged tRNAs is modified by one or more mutations in the coding region of the RNAI gene and one or more corresponding mutations in the RNAII gene, said mutation(s) resulting in one or more base exchanges in loop 1 and/or loop 2 and/or loop 3 of RNAI and RNAII.

BRIEF DESCRIPTION OF THE DRAWINGS/FIGURES

FIG. 1 shows the fermentation process using the plasmid, pET11achSOD, in *E. coli* HMS 174 (DE3). The total and specific production of the recombinant protein (SOD), along with the production rate, $q_p$, is shown. Also shown are the total bacterial dry matter (BDM) and the plasmid copy number (PCN).

DETAILED DESCRIPTION OF THE INVENTION

In particular, it was an object of the invention to provide an expression system in which plasmid copy number, after induction of the expression system, is limited with respect to uncontrolled amplification, in order to keep the metabolic burden below lethal doses.

It was a further object of the invention to increase plasmid replication rates and thus the yield of plasmid DNA in plasmid production processes.

To solve the problem underlying the invention, the mechanism of ColE1-type replication was utilized. Specifically, a genetic approach was taken to alter, preferably decrease or completely abolish, the degree of homology of the ColE1 origin of replication to uncharged tRNAs. In an alternative approach, a random library was created in order to select for plasmids with altered replication behavior, e.g., high plasmid copy number.

The term "mutation" encompasses both mutations that increase and mutations that decrease homology of RNAI and RNAII to uncharged tRNAs.

In order to maintain the secondary structure and melting temperature of RNAI and RNAII as far as possible in order not to impair replication, the mutations are preferably complementary base exchanges, i.e., A→T, T→A, C→G, G→C mutations. Other mutation(s) may also be present, provided the mechanism of replication is not impaired.

As opposed to the ColE1 vector according to International Appl. No. WO 89/07141, which contains a mutation in the RNAII gene and, due to its position, consequently in the promoter of the RNAI gene, the vector of the invention comprises a mutation in the coding region, more specifically in the loop regions of both the RNAI and RNAII gene, which are homologous to uncharged tRNAs. The present invention thus provides a novel strategy to deliberately manipulate the degree of homology and ultimately tune the rate of plasmid replication.

In the meaning of the present invention, the term "loop" preferably encompasses the unpaired loop structure of RNAI or RNAII; however, this term is not strictly limited to the mere loop region, but may also comprise the adjacent nucleotides of the stem region, preferably not more than two nucleotides.

The mutation(s) may be a single base exchange in either loop 1, loop 2 or loop 3 or a single or any number of base exchanges, including all base exchanges, in loop 1 and/or loop 2 and/or loop 3.

Preferably, the mutation(s) are in loop 2, which is the region with the highest homology to uncharged tRNAs.

The desired mutations in the loop(s) of the RNAI and RNAII gene may be obtained according to conventional mutation and cloning techniques.

In one embodiment, they can be obtained as follows: starting from either the RNAI or the RNAII gene or a fragment thereof as a template, a PCR reaction is carried out which employs as primers two oligodesoxyribonucleotides, one or both carrying the desired mutation(s). Preferably, the PCR reaction is a two-step PCR. In the first step, two overlapping fragments are amplified, one of which contains the desired mutation in the primer sequence between a restriction site that is designed for connecting the fragments, and the primer binding site. Next, the amplified fragments are digested with the relevant restriction enzyme, ligated and used as a template in the next PCR amplification step. In this step, the same primers as in the first step, which do not contain the newly-introduced restriction site, are used, which have been selected to bind upstream and downstream of the nearest unique restriction sites in the individual plasmid.

Due to the complementarity of the RNAI and RNAII genes, in the preparation of the vector, both genes or fragments thereof are equally suitable as a template for the PCR amplification. With the given complementarity, any mutation(s) in one or more loops of either of the genes will result in the corresponding mutation in the other, complementary gene; in the preferred method described above, the primer containing the mutation(s) not only serves for elongation by the polymerase, but also as a template for the DNA polymerase, thus yielding the complementary strand containing the mutation(s). Depending on whether the RNAI or RNAII gene is used as a template, RNAII or RNAI will automatically carry the complementary mutation.

Preferably, a plasmid containing the entire RNAI and RNAII genes is used as a template. Alternatively, a DNA molecule encoding the entire RNAI or RNAII gene may be used. The RNAI and RNAII genes were described by Tomizawa et al. (1977).

In the case that an RNAI or RNAII gene fragment is used as a template, the fragment must have a size that is sufficient to contain all elements required, i.e., the sequence to be mutated, the primer binding site and, optionally, one or more restriction sites. Preferably, the fragment comprises one or more loops (each of them consisting of approximately 7 nucleotides) and a primer binding site (approximately 18 nucleotides), i.e., the minimal size of a suitable fragment is approximately 25 to 30 nucleotides.

In a preferred embodiment of the invention, the mutations are selected, in terms of site(s) and number(s), with the aim of substantially changing the degree of homology to as many uncharged tRNA species as possible.

Thus, in an embodiment of the invention, the modification of RNAI and RNAII is carried out by starting from a modification in loop 2, i.e., the loop with the highest homology, said modification representing the exchange of as many positions as possible. By way of example, as shown in the experiment of Example 1, loop 2 may be modified by replacing six of its seven nucleotides, leaving one base (position 693 in plasmid ColE1, Genbank GI 9507253) unchanged and thus available as part of the new restriction site, preferably a NcoI site. The bases are replaced by their respective complementary bases.

By this approach, if desired, homology to all uncharged tRNAs can be completely abolished. Therefore, this approach provides a maximum flexibility for the production of a great variety of recombinant proteins of interest independent of their amino acid sequence, in particular through control of plasmid replication maintaining cell viability during expression. In this case, plasmid amplification is subject only to the control by the ColE1 specific replication mechanism and independent of metabolic fluctuations of the host cell; in this case, plasmid copy number remains essentially constant throughout the fermentation process.

Alternatively to completely abolishing the homology between RNAI and RNAII and uncharged tRNAs, this homology may be modified, i.e., increased or decreased, only to a certain desired degree. For some applications, e.g., if the yield of the product is unsatisfactory because the potential of the expression machinery is not fully exploited due to the decreased plasmid copy number and thus suboptimal amount of plasmids ("gene dosage"), it may be desirable to increase expression rates by slightly increasing plasmid copy number. This can be achieved by selectively maintaining sequence homology to some uncharged tRNAs, in particular to rare tRNAs. The sequence homologies for specific uncharged tRNAs is known from the literature (Zavachev, L. and Ivanov, I., *J. Theor. Biol.* 131:235–241 (1988)). This strategy may also be useful for influencing the rate of protein synthesis such that the product is either present in the form of inclusion bodies or in soluble form. By way of example, a certain degree of plasmid amplification may lead to the formation of inclusion bodies, while a slight decrease may favor the formation of soluble product.

For some applications it is advantageous to drastically increase plasmid copy number by increasing the sequence homology of RNAI and RNAII to uncharged tRNAs, in particular for plasmid DNA production. The mutations required to increase sequence homology are also known in the literature (Zavachev, L. and Ivanov, I., *J. Theor. Biol.* 131:235–241 (1988)) and can be carried out according to the same principles as described for the decrease of sequence homology.

For an individual application and/or product, the process can be optimized by experimentally testing a range of mutations. Suitable experiments may be conducted as follows: a plasmid or a series of plasmid candidates carrying the mutation(s) to be tested are transfected into appropriate bacterial host cells, grown under suitable conditions in a small scale, e.g., in shake flasks, and the fermentation process is monitored with respect to the parameters of interest, in particular growth, product yield and quality, plasmid copy number.

Another embodiment, which is particularly useful to obtain a wide range of sequence modifications, is to randomly mutate one or more positions of loop 1 and/or loop 2 and/or loop 3, thus generating a library which may be used for the construction of an expression vector selected for any desired property of the expression system. By way of example, a plasmid candidate may be selected due to certain selection parameters that are most relevant for recombinant protein production, e.g. growth rate, productivity and viability; the process is carried out in an standard experimental setup as described above.

Furthermore, this approach allows for efficient tuning of recombinant protein expression rate based on PCN manipulation. Provided the gene of interest is present in the vector containing the library, the selected plasmid will always be optimal for expression of the gene of interest.

While during normal fermentations an almost tenfold increase in plasmid copy number (PCN) after induction is being observed, according to the present invention the homology between tRNAs and RNAII being decreased or abolished. This has the effect that a larger pool of non-inhibited RNAI molecules is free to interact with RNAII. Thus, the mechanism of replication is detached from high pools of uncharged tRNAs caused by metabolic overload due to expression of recombinant protein. Detaching the mechanism of plasmid replication from metabolic stress related to recombinant protein expression results in higher yield of recombinant protein.

Since the base exchanges according to the present invention are present both in RNAI and RNAII, which results in a change in homology to all tRNAs, the composition of uncharged tRNAs (depending on the recombinant product) is not relevant for this approach.

In addition to the modified ColE1 replication system, the expression vector of the invention comprises the elements required for protein expression, i.e. expression control sequences operatively linked to the cDNA sequence encoding the protein of interest, including promoter, translation initiation region, selection markers (e.g. antibiotic resistance markers), restriction sites for insertion of the DNA encoding the protein of interest, etc.

Preferably, the expression vector of the invention is derived from one of the following vectors:

pMB1 (Bolivar, F., et al., *Gene* 2:95–113 (1977));

pBR322 (Covarrubias, L., et al., *Gene* 13:25–35 (1981); available from MBI Fermentas catalogue number #SD0041; GenBank/EMBL sequence accession numbers J01749, K00005, L08654, M10282, M10283, M10286, M10356, M10784, M10785, M10786, M33694, V01119);

pUC18 (Yanisch-Perron, C., et al., *Gene* 33:103–119 (1985); GenBank/EMBL sequence accession number L09137; available from MBI Fermentas catalogue number #SD0061);

pUC19 (GenBank/EMBL sequence accession number L09136. available from MBI Fermentas #SD0051);

pTZ19R (GenBank/EMBL sequence accession number Y14835; available from MBI Fermentas, catalogue number #SD0141);

pTZ19U (available from MBI Fermentas, catalogue number #SD0161; GenBank/EMBL sequence accession number Y14835);

pBluescriptIIKS(−)(Alting-Mees, M. A. and Short, J. M., *Nucleic Acids Res.* 17:9494 (1989); GenBank/EMBL sequence accession number X52329);

pBluescriptII KS(+)(Alting-Mees, M. A. and Short, J. M., *Nucleic Acids Res.* 17:9494 (1989); GenBank/EMBL sequence accession number X52327);

pBluescriptII SK(-)(Alting-Mees, M. A. and Short, J. M., *Nucleic Acids Res.* 17:9494 (1989); GenBank/EMBL sequence accession number X52330.

pBluescriptII SK(+)(Alting-Mees, M. A. and Short, J. M., *Nucleic Acids Res.* 17:9494 (1989); GenBank/EMBL sequence accession number X52328).

With regard to the protein of interest, there are no limitations in terms of sequence, as long as the expression of the plasmid in *E. coli* renders a functional protein.

In the experiments of the present invention, the cDNA encoding human Cu—Zn superoxide dismutase was used. From a vector carrying this cDNA, a highly soluble, 32 kDa dimeric protein can be produced which consists of 153 amino acids and is released into the cytoplasm (Cserjan-Puschmann, M., et al., *Appl. Microb. Biotechnology* 53:43–50 (1999)).

Any bacterial host cell that is compatible with ColE1 type plasmids may be used, preferably *E. coli* strains, in particular strain HMS 174 (DE3) (Studier, F. W. and Moffat B. A., *J. Mol. Biol* 189:113–130 (1986)), or Salmonella strains.

In a further embodiment, the present invention relates to a host cell transformed with the expression vector carrying the modified ColE1 replication.

For transformation of the host strain, any conventional technique may be used, e.g., electroporation or calcium chloride or calcium precipitation.

In a further embodiment, the present invention relates to a method for producing a recombinant protein of interest, wherein a *E. coli* host cell is transformed with an expression vector having a ColE1 replication system with a mutation in one or more loops of the RNAI and RNAII gene, grown under suitable conditions and the protein of interest is recovered. The invention accelerates recombinant protein production process development by providing a tool for compensating the interference resulting from expression of recombinant proteins with the host metabolism. The method of the invention is particular advantageous in fed batch fermentation processes, i.e. processes wherein the addition of nutrients is coupled to the increase of biomass. To fully exploit the advantages of fed batch processes, which can be run over extended periods of time and thus result in higher biomass production and overall process economy than classical batch processes, a stable and regulatable expression system is required. This need can be beneficially met by the use of the expression vector of the invention.

Furthermore, since alterations of the sequence of one or more loops of the ColE1 RNA I and RNA I can serve to drastically increase plasmid replication rates, the vectors are very useful for production the production of plasmids, e.g., for use in gene therapy. The advantages of the present invention lie in the possibility to decrease the stability of the so-called RNA I/RNA II "kissing complex" and thus to enhance plasmid replication rates.

EXAMPLE 1

The plasmid used in the experiments was pET11a (derivative of pUC19 from Stratagene). This plasmid contains the beta-lactamase gene for ampicillin resistance. The recombinant protein expression in this plasmid is controlled by the efficient T7 RNA polymerase. The lac operator is situated between the T7 promoter and translation initiation sequences. This results in repression in the absence of the inducer IPTG. The pET11a-SOD plasmid contains a cDNA gene coding for the recombinant protein human Cu-Zn superoxide dismutase (hSOD), a highly soluble, 32 kDa dimeric protein of 153 amino acids, which is non-toxic for the cell and released into the cytoplasm (Cserjan-Puschmann, M., et al., *Appl. Microb. Biotechnology* 53:43–50 (1999)).

The bacterial strain used for plasmid propagation and expression of SOD was *Escherichia coli* HMS174(DE3) (Studier, F. W. and Moffat B. A., *J. Mol. Biol.* 189:113–130 (1986)). This strain has the T7 polymerase integrated in the chromosomal DNA. The T7 polymerase is essential for expression of the recombinant protein. Transformants were selected on amp plates (Antibiotic medium LB, containing 100 pg/ml ampicillin) (Maniatis, T., *Molecular Cloning: A Laboratory Manual*, Cold Spring Harbor Laboratory, Cold Spring Harbor, N.Y. (1982)).

The transformation technique used in these experiments was electroporation using a Bio-Rad Gene Pulser. The primers were obtained from Metabion (Martinsried, Germany) in the form of a vacuum-dried powder, which was dissolved in water to obtain stock solutions with the concentration of 100 pmol/µl. PCR was carried out using a Thermoblock (T-gradient, Biometra, Germany) with heatable cover Dynazyme EXT polymerase 1 u/µl (Finnzymes), 10×Mg-free buffer and 10 mM MgCl (supplied) 1 mM dNTP, DMSO and distilled water.

Primers used were pET11a-114back (SEQ ID NO:1), pEZ11a656 for (SEQ ID NO:2), RNAI-Ncoback (SEQ ID NO:3) and RNAI-Nco for (SEQ ID NO:4). Restriction endonucleases, Lambda markers, T4-Ligase, Calf intestine phosphatase, were obtained from MBI-Fermentas and used according to their recommendations.

The fermentor used was a 20-liter fermentor from MBR Bioreactor AG (Wetzikon, Switzerland), with an MBR IMCS-2000 controller connected to it. The working volume of the fermentor was about 12 liters.

Feed media used: The amount of feed media pumped into the system during fed-batch state was measured by continuously weighing the vessel. The feed pump was regulated to give a constant growth rate of $\mu=0.1$. Antifoam addition triggered by a conductivity sensor. No contact with exterior, implying no risk of fermentor contamination. The batch medium used was a semi-synthetic medium, containing small amounts of tryptone and yeast extract to facilitate growth at the start of the batch. The components were mixed together in a total volume of about 4 liters (4000 g). But to avoid precipitations, chemicals with the same number (see # Table 1 below) were first dissolved in distilled water separately. The glucose solution was filled out with distilled water to 300 g and autoclaved separately. Subsequently all but the glucose solution were mixed together in the given order, and filled out with distilled water to 3700 g.

TABLE 1

Composition of the batch medium (4000 g). Values given in grams, if not otherwise stated.

| # | Weight (g) | Chemical |
| --- | --- | --- |
| 1 | 12 | Potassium dihydrogen phosphate |
| 1 | 24 | Di-Potassium hydrogen phosphate Trihydrate |
| 2 | 2 | Tryptone (Oxoid Ltd. Hampshire, UK) |
| 2 | 1 | Yeast extract |
| 3 | 5 | Tri-Sodium citrate dihydrate |
| 3 | 2 | Magnesium sulfate heptahydrate |
| 4 | 0.2 | Calcium chloride dihydrate |
| 5 | 1000 | Trace element solution [µl] |
| 6 | 80 | Copper(II) chloride dihydrate [mg] |
| 6 | 64 | Zinc sulfate heptahydrate [mg] |
| 7 | 9 | Ammonium sulfate |
| 7 | 7.4 | Ammonium chloride |
| 8 | 66 | Glucose Monohydrate |

TABLE 2

Composition of the feeding medium (6000 g) for fed-batch state. Values given in grams, if not otherwise stated

| # | Weight (g) | Chemical |
|---|---|---|
| 1 | 18.00 | Potassium dihydrogen phosphate |
| 1 | 36.00 | Di-Potassium hydrogen phosphate Trihydrate |
| 2 | 51.57 | Tri-Sodium citrate dihydrate |
| 2 | 20.63 | Magnesium sulfate heptahydrate |
| 3 | 2.06 | Calcium chloride dihydrate |
| 4 | 10313.71 | Trace element solution [μl] |
| 5 | 825.10 | Copper(II) chloride dihydrate [mg] |
| 5 | 660.08 | Zinc sulfate heptahydrate [mg] |
| 6 | 0.6 | Antifoam |
| 7 | 92.82 | Ammonium sulfate |
| 7 | 76.32 | Ammonium chloride |
| 8 | 680.70 | Glucose Monohydrate |

The Koch test was performed to determine the fraction of bacterial cells containing plasmids, and to determine whether the plasmid-carrying cells grow on plates containing the inducer IPTG, the latter indicating whether the plasmid-carrying cells produce SOD in "normal" amounts after induction.

The bacterial dry mass (BDM) gives the total amount of dry matter.

For each sample, a glass beaker was dried overnight at 105° C., cooled in an exsiccator and then weighed on an analytical scale.

PCN can be calculated from correlating the sizes (number of basepairs) of the genomic DNA and the plasmid DNA.

For plasmid DNA preparation, the cell pellet from sample preparation was resuspended in 150 μl solution 1 (50 mM glucose, 10 mM EDTA, 25 mM Tris-HCl pH 8.0) 200 μl SDS was added (0.5% SDS solution (ICN Biochemicals) 50 μl lysozyme (Sigma) was added, the preparation was mixed and incubated for 10 min at 37° C., the solution homogenized by vortexing. The samples were stored on ice until fluorescence measurement with a spectrofluorometer (Hitachi F-2000).

For determining the amount of plasmid DNA, the DNA in the cell pellet was purified with the GFX kit (MBI, Fermentas) according to the supplier's instructions, with the following modifications: after the lysis step a known amount (~2 μg) pUC 19 was added as internal standard. Elution of the DNA in 50 μl water was followed by a linearization of the plasmid with Hind III for 1 hour at 37° C. The sample with the restriction-digested DNA was transferred to a sample vial for capillary electrophoresis, avoiding air bubbles. The samples were loaded into an autosampler. The capillary was calibrated by flushing with buffer for 15–20 min. Absorbance detection occurred at 260 nm and 280 nm by a diode array. After the analysis the capillary was flushed with buffer and stored at 4° C.

The amount of chromosomal DNA was calculated by subtracting the amount of plasmid DNA/mg BDM from the total DNA content/mg BDM. As the amount of internal standard added was known, the PCN could, according to Breuer, S., et al., *Electrophoresis* 19:2474–78 (1998), be calculated by the following formulas:

$$\text{Plasmid DNA in sample} = \frac{\text{Internal standard added}}{\text{Measured internal standard}} \times \text{Measured plasmid DNA}$$

$$PCN = \frac{\sum \text{Chromosomal basepairs} \times \text{Amount of plasmid DNA/mg BDM}}{\sum \text{Plasmid basepairs} \times \text{Amount of chromosomal DNA/mg BDM}}$$

For determination of the amount of SOD, capturing antibodies (SOD monoclonal antibody clone 30F11 available from Novocastra Laboratories (Ltd, UK) were diluted 1:100 in coating buffer (200 μg/ml). 100 μl of diluted antibody solution were transferred to each well on microtiter plate, incubated at 4° C. overnight, or at room temperature for at least 2 hours. The plate was washed three times with washing buffer and the buffer removed by knocking the plate gently. Sample and standard were diluted in 1:2 steps by pipette robot on dilution plate. 50 μl of each different dilution were transferred (by robot) to the antibody coated plate and incubated for 1 hour at room temperature.

The plate was washed with washing buffer. Conjugated antibody was diluted 1:500 in dilution buffer Porstmann, T., et al., *Clinaica Chimica Acta* 171:1–10 (1988).

Mutations within the origin of replication are indicated in Table 3 (the table lists the changed positions, the numbers referring to the complete ColE1 sequence according to GI="9507253" Genbank):

TABLE 3

| 692 | G → C |
|---|---|
| 694 | T → A |
| 695 | A → T |
| 696 | C → G |
| 697 | C → G |
| 698 | A → T |
| 699 | A → T |
| 700 | C → G |

The fermentation process using the plasmid in *E. coli* HMS 174 (DE3) pET11achSOD is shown in FIG. 1. The total and specific production of the recombinant protein (SOD), along with the production rate, $q_p$, is shown. Also shown are the total bacterial dry matter (BDM) and the plasmid copy number (PCN). As opposed to standard processes (e.g., as described by Cserjan-Puschmann, M., et al, *Appl. Microb. Biotechnology* 53:43–50 (1999)), it was observed that the PCN is kept rather constant even after induction at the 45$^{th}$ hour.

The results of the Koch tests and the plasmid copy numbers are shown in the following:

TABLE 4

| Fermentation time [h] | CFU [ml-1] | CFU on ampicillin plate | Plasmid carrier [%] | IPTG insens. plasmid carrier | PCN |
|---|---|---|---|---|---|
| 31 | 5.5 × 10$^9$ | 5.13 × 10$^9$ | 93.33 | 1.12 × 10$^7$ | |
| 37 | 1.98 × 10$^{10}$ | 1.96 × 10$^{10}$ | 98.99 | 6.67 × 10$^6$ | 50 |
| 41 | | | | | 48 |
| 45 | | | | | 42 |
| 46 | | | | | 38 |
| 47 | 3.03 × 10$^{10}$ | 2.66 × 10$^{10}$ | 87.69 | 1.63 × 10$^6$ | 45 |
| 48 | | | | | 44 |
| 50 | | | | | 51 |
| 52 | 1.89 × 10$^{10}$ | 1.43 × 10$^{10}$ | 75.70 | 1.38 × 10$^6$ | 34 |

EXAMPLE 2

The plasmid used in the experiments was pET11a-SOD as described in Example 1. The bacterial strain used for plasmid propagation and expression of SOD was *Escherichia coli* HMS174(DE3), as described in Example 1. All manipulations of bacteria and plasmid DNA were carried out as described in Example 1. Oligonucleotides and enzymes were obtained from the same sources as described in Example 1.

Primers used were pet11a-Sca-I-for (SEQ ID NO:5), pet11a-AlwN-I (SEQ ID NO:6), pet11a-Xba-I-back (SEQ ID NO:7) and RNA-I-randomXba-I-back (SEQ ID NO:8).

To screen for the best candidates in the pool of different clones, two approaches were used:

1. Selection of Cells with a High Plasmid Copy Number

Cells with a high PCN should have a higher resistance against ampicillin. The pool of bacteria was plated on LB-agar petri dish containing either 0.1, 1 or 10 mg/ml ampicillin. 10 colonies of the 10 mg/ml LB-Amp-plate were picked and the sequence analyzed. The result revealed 7 clones (see Table 5) that were different with regard to the sequence of loop 2 of RNA I and RNA II.

TABLE 5

|  | RNAII | RNAI |
| --- | --- | --- |
| ColE1Mut1 | ATCTACA | TGTAGAT |
| ColE1Mut9 | ATCTACA | TGTAGAT |
| ColE1Mut2 | TGGATAC | GTATCCA |
| ColE1Mut3 | TTCACCC | GGGTGAA |
| ColE1Mut4 | CTGTATC | GATACAG |
| ColE1Mut5 | AACATCC | GGATGTT |
| ColE1Mut7 | AACATCC | GGATGTT |
| ColE1Mut8 | AACATCC | GGATGTT |
| ColE1Mut6 | GCTAGCG | CGCTAGC |
| ColE1Mut10 | ACTGAAG | CTTCAGT |

The second screening criteria was the stability of the plasmids. Bacteria containing the plasmid pool were cultivated in shake flasks at 37° until OD=2 using a synthetic medium without ampicillin. After three passages (corresponding to approximately 20 generations) bacteria from the last passage were spread onto a LB-amp plate to select for the bacteria that still contained a plasmid, single colonies were picked for sequence analysis.

The result of this screen is shown in Table 6:

TABLE 6

|  | RNAI | RNAII |
| --- | --- | --- |
| ColE1Mut11 | TTATGAG | CTCATAA |
| ColE1Mut12 | TTGCCAC | GTGGCAA |
| ColE1Mut13 | CTTACGA | TCGTAAG |
| ColE1Mut14 | CATGCAA | TTGCATG |
| ColE1Mut15 | GTGACAA | TTGTCAC |
| ColE1Mut16 | CCGACAA | TTGTCGG |
| ColE1Mut17 | GGGGAAA | TTTCCCC |
| ColE1Mut18 | CTCGCCT | AGGCGAG |
| ColE1Mut19 | AGGCCCT | AGGGCCT |
| ColE1Mut20 | TTGGTAG | CTACCAA |
| ColE1Mut21 | ATAGCAG | CTGCTAT |
| ColE1Mut22 | TTGAGAT | ATCTCAA |
| ColE1Mut23 | TTGGTAG | CTACCAA |
| ColE1Mut24 | TTAGCGT | ACGCTAA |
| ColE1Mut25 | TTCTGCT | AGCAGAA |
| ColE1Mut26 | TTGCCAT | ATGGCAA |
| ColE1Mut27 | GATGGTT | CTACCAA |
| ColE1Mut28 | TTTTCGC | GCGAAAA |
| ColE1Mut29 | TACCCCC | GGGGGTA |
| ColE1Mut30 | CATTCGA | TCGAATG |
| ColE1Mut31 | GTTCCGA | TCGGAAC |
| ColE1Mut32 | GTAGCCA | TGGCTAC |
| ColE1Mut33 | ACTCTAA | TTAGAGT |

TABLE 6-continued

|  | RNAI | RNAII |
| --- | --- | --- |
| ColE1Mut34 | CTTGGAA | TTCCAAG |
| ColE1Mut35 | CCCCCAA | TTGGGGG |
| ColE1Mut36 | TTGGTGT | ACACCAA |
| ColE1Mut37 | TTGCAAT | ATTGCAA |
| ColE1Mut38 | TTGCGAG | CTCGCAA |
| ColE1Mut39 | TGGTCAG | CTGACCA |
| ColE1Mut40 | ATGTCAA | TTGACAT |
| ColE1Mut41 | CACCCAA | TTGGGTG |
| ColE1Mut42 | GCGGAAA | TTTCCGC |
| ColE1Mut43 | GTGTCAA | TTGACAC |
| ColE1Mut44 | TCGCCNG | CNGGCGA |
| ColE1Mut45 | TCGCCNG | CNGGCGA |
| ColE1Mut46 | TTTCCCG | CGGGAAA |
| ColE1Mut47 | TACCCCG | CGGGGTA |
| ColE1Mut48 | TCGCTAG | CTAGCGA |
| ColE1Mut49 | TCTTGCC | GGCAAGA |
| ColE1Mut50 | TTGGTAC | GTACCAA |
| ColE1Mut51 | TCACCAC | GTGGTGA |
| ColE1Mut52 | CCGCGAA | TTCGCGG |
| ColE1Mut53 | ACGCAAA | TTTGCGT |
| ColE1Mut54 | CTGAACT | AGTTCAG |
| ColE1Mut55 | CCCCCAT | ATGGGGG |
| ColE1Mut56 | CCCCCAT | ATGGGGG |
| ColE1Mut57 | TTTGCCG | CGGCAAA |
| ColE1Mut58 | TTCGCCG | CGGCGAA |
| ColE1Mut59 | TTCGCCG | CGGCGAA |
| ColE1Mut60 | GAGGTAG | CTACCTC |
| ColE1Mut61 | TGTCCAG | CTGGACA |
| ColE1Mut62 | CCTCTAA | TTAGAGG |
| ColE1Mut63 | ACGCAAA | TTTGCGT |
| ColE1Mut64 | TGGGTAG | CTACCCA |
| ColE1Mut65 | TCTTCAC | GTGAAGA |
| ColE1Mut66 | TTAGCAC | GTGCTAA |
| ColE1Mut67 | TTGGTAG | CTACCAA |

The fermentor and accessories used in this screen were the same as described in Example 1. Feed media and growth rate were the same as described in Example 1.

The PCN was determined and calculated as described in Example 1. The behaviour of the clone candidates with regard to their PCN was characterized in fed batch cultivations. The results of promising candidates are shown in Table 7; the PCN of different clones is shown for the uninduced and the induced state.

TABLE 7

|  | uninduced | induced 3 h | induced 5 h |
| --- | --- | --- | --- |
| ColE1WT | 54 | 129 | 298 |
| ColE1Mut9 | 750 | 2560 | 600 |
| ColE1Mut22 | 136 | 243 | 380 |
| ColE1Mut54 | 34 | 63 | 93 |

The clone ColE1Mut9 (and ColE1Mut1, which has the same sequence) turned out to be a very promising candidate for plasmid production. A plasmid copy number of 750 represents an approximately 14fold increase, as compared to the wild type ColE1 plasmid.

PCN of Clone ColE1Mut22 was also higher (factor 2.5).

The lower PCN of clone ColE1Mut54 could be beneficial for recombinant protein production due to a lower metabolic load.

What is claimed is:

1. An expression vector having a Col E1 replication system, wherein the homology of the RNAI and RNAII of the ColE1 origin of replication to one or more uncharged tRNAs is modified by one or more mutations in the coding region of the RNAI gene and one or more corresponding mutations in the RNATI gene, said mutation(s) resulting in one or more base exchanges in loop 1 and/or loop 2 and/or loop 3 of RNAI and RNAII.

2. The expression vector of claim 1, which is derived from a vector selected from pMB1, pBR322, pUC18, pUC19, pTZ19R, pTZ19sU, pBluescriptIIKS(+/−) and pBluescriptIISK(+/−).

3. The expression vector of claim 1, wherein said mutation results in a decrease or abolishment of RNAI/RNAZII homology to one or more uncharged tRNAs.

4. The expression vector of claim 3, wherein said mutation is in loop 2 of RNAI and RNAII.

5. The expression vector of claim 4, wherein loop 2 of RNAI and RNAII is modified by a mutation of essentially its complete sequence.

6. The expression vector of claim 5, wherein six of seven bases of loop 2 are replaced by their respective complementary bases.

7. The expression vector of claim 6, wherein loop 2 of RNAI contains the sequence TGTAGAT in place of the wildtype sequence and wherein loop 2 of RNAII contains the sequence ATCTACA in place of the wild type sequence.

8. The expression vector of claim 6, wherein loop 2 of RNAI contains the sequence CUGAACU in place of the wildtype sequence UUGGUAG and wherein loop 2 of RNAII contains the sequence AGUUCAG in place of the wild type sequence CUACCAA.

9. A bacterial host cell transformed with a vector of anyone of claims 1 to 8.

10. The host cell of claim 9, which is an E-coli cell.

11. The host cell of claim 10, which is a cell of E. coli coli strain HMS174.

12. A method of producing a recombinant protein of interest in E. coli comprising:
   (a) transforming E. coli with the expression vector of any one of claims 1 to 8 containing a gene encoding the recombinant protein of interest; and
   (b) growing a culture of said E. Coli transformed with said expression vector under conditions which cause the expression of said recombinant protein.

13. A method of producing plasmid DNA in E. coli comprising:
   (a) transforming into E. coli with the expression vector of any one of claims 1 to 8; and
   (b) growing a culture of said E. coli transformed with said expression vector under conditions which allow replication of said expression vector.

14. A method for producing a protein of interest, wherein a vector of any one of claims 1 to 8, which contains a DNA encoding the protein operatively linked to expression control sequences, is used to transform a bacterial host cell compatible with the Col E1 replication system, the host cell is grown under suitable conditions and the protein of interest is recovered and purified.

* * * * *

SEQUENCE LISTING

<160> NUMBER OF SEQ ID NOS: 8

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 1
gacttatcgc cactggcag                                              19

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 2
gagcgtgaca ccacgatgc                                              19

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 3
gatgatccat ggtcttgatc cggcaaacaa ac                               32

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 4
gatgatccat ggttgtcttt ttccgaaggt aactgg                           36

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 5
gacactgacc actcatgagt tggttc                                      26

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 6
gacttatcgc cactggcag                                              19

<210> SEQ ID NO 7
<211> LENGTH: 31

```
<212> TYPE: DNA
<213> ORGANISM: Artificial Sequence
<220> FEATURE:
<223> OTHER INFORMATION: Description of Artificial Sequence: Primer

<400> SEQUENCE: 7
ggtagctcta gatccggcaa acaaaccacc g                                    31

<210> SEQ ID NO 8
<211> LENGTH: 42
<212> TYPE: DNA
<213> ORGANISM: Artificial Sequence
<220> FEATURE:
<221> NAME/KEY: Unsure
<222> LOCATION: (14)..(20)
<223> OTHER INFORMATION: May be any nucleic acid
<223> OTHER INFORMATION: Description of Artificial Sequence: Primer

<400> SEQUENCE: 8
gccggatcta gagnnnnnnn ctcttttcc gaaggtaact gg                         42
```